United States Patent
Buchecker et al.

[11] Patent Number: 5,965,761
[45] Date of Patent: Oct. 12, 1999

[54] PHOTOACTIVE SILANE DERIVATIVES FOR LIQUID CRYSTALS

[75] Inventors: Richard Buchecker, Zürich, Switzerland; François Herzog, Richwiller; Guy Marck, Schlierbach, both of France; Andreas Schuster, Freiburg, Germany

[73] Assignee: Rolic AG, Zug, Switzerland

[21] Appl. No.: 08/957,096

[22] Filed: Oct. 24, 1997

[30] Foreign Application Priority Data

Oct. 28, 1996 [EP] European Pat. Off. ............ 96 117 246

[51] Int. Cl.$^6$ ................................. C07F 7/08; C07F 7/10
[52] U.S. Cl. .................. 556/440; 556/415; 556/438; 556/420; 556/419; 556/489; 556/445; 556/413; 546/14; 544/229; 549/214; 427/489; 427/407.2; 427/387; 106/287.1; 106/287.11; 106/287.13; 106/287.16
[58] Field of Search ..................... 556/440, 415, 556/438, 420, 419, 489, 445, 413; 546/14; 544/229; 549/214; 427/489, 407.2, 387; 106/287.1, 287.11, 287.13, 287.16

[56] References Cited

U.S. PATENT DOCUMENTS

| | | |
|---|---|---|
| 4,861,906 | 8/1989 | Varapath et al. . |
| 4,918,200 | 4/1990 | Arkles . |
| 4,974,941 | 12/1990 | Gibbons et al. . |
| 5,093,511 | 3/1992 | Yoshida et al. ........................ 556/440 |
| 5,315,022 | 5/1994 | Yoshida et al. ........................ 556/437 |
| 5,348,684 | 9/1994 | Hemmerling et al. .................. 556/445 |
| 5,399,738 | 3/1995 | Wolter et al. ........................... 556/420 |
| 5,792,881 | 8/1998 | Wolter et al. ........................... 556/429 |
| 5,869,276 | 2/1999 | Dauth et al. ............................ 556/440 |

FOREIGN PATENT DOCUMENTS

| | | |
|---|---|---|
| 0 611 786 A1 | 2/1994 | European Pat. Off. . |
| 0 611 981 A1 | 2/1994 | European Pat. Off. . |
| 0 689 084 A1 | 6/1995 | European Pat. Off. . |
| 689 065 A1 | 6/1995 | European Pat. Off. . |
| 0 753 785 A1 | 7/1996 | European Pat. Off. . |

OTHER PUBLICATIONS

Schadt, et al,. "Surface–Induced parallel Alignment of Liquid Crystals by Linearly Polymerized Photopolymers," *Jpn. J. Appl. Phys.*, vol. 31, pp. 2155–2164 (1992).

Tomita, et al., "Command surfaces 15 [1]. Photoregulation of Liquid Crystal Alignment by Cinnamoyl Residues on a Silica Surface," *Liquid Crystals*, vol. 20, No. 2, pp. 171–176 (1996).

*Primary Examiner*—Paul F. Shaver
*Attorney, Agent, or Firm*—Finnegan, Henderson, Farabow, Garrett & Dunner, L.L.P.

[57] ABSTRACT

The invention provides novel cross-linkable, photoactive silane derivatives and mixtures with 3-aryl-acrylic acid esters and amides. The present invention also provides orienting layers for liquid crystals, and non-structured and structured optical elements and multi-layer systems based on the silane mixtures and derivatives.

16 Claims, No Drawings

PHOTOACTIVE SILANE DERIVATIVES FOR LIQUID CRYSTALS

FIELD OF THE INVENTION

The invention provides novel cross-linkable, photoactive silane derivatives and mixtures with 3-aryl-acrylic acid esters and amides. The silane derivatives can be used as orienting layers for liquid crystals and for the production of non-structured and, respectively, structured optical elements and multi-layer systems.

BACKGROUND OF THE INVENTION

The orienting layer is of particular significance in (electro-optical) liquid crystal devices. It serves the purpose of guaranteeing a uniform and disturbance-free alignment of the molecular axes.

Uniaxially rubbed polymer orienting layers, such as e.g. polyimide, are usually used for the orientation of liquid crystal molecules in liquid crystal indicators (LCD's). The direction of rubbing provides the orienting direction in this procedure. However, some serious disadvantages are associated with the rubbing and these can severely influence the optical quality of liquid crystal indicators. Thus, by rubbing, dust is produced which can lead to optical failure in the display. At the same time, the polymer layer becomes electrostatically charged, which, for example, in the case of Thin Film Transistor (TFT)-TN LCD's can lead to the destruction of the thin layer transistors which lie below. For these reasons the yield of optically faultless displays in LCD production has hitherto not been optimal.

A further disadvantage of rubbing is that it is not possible to produce in a simple manner structured orienting layers, since the direction of orientation can not be varied locally by rubbing. Accordingly, mainly uniformly directed layers of large area can be produced by rubbing. Structured orienting layers are, however, of great interest in many areas of display technology and integrated optics. For example, the viewing angle dependence of Twisted Nematic (TN) LCD's can be improved with them.

Orienting layers in which the orienting direction can be produced by irradiation with polarized light have been known for some time. Thereby, the problems inherent in rubbing can be avoided. In addition, there exists the possibility of producing a different orienting direction in a regional manner and thus to structure the orienting layer.

One possibility for the structured orienting of liquid crystals utilises the isomerizing capability of certain dye molecules in order to photochemically induce a preferred direction by irradiation with polarized light of suitable wavelength. This is achieved, for example, by admixing a dye with an orienting polymer and then irradiating with polarized light. Such a guest/host system is described, for example, in U.S. Pat. No. 4,974,941. In this system azobenzenes are incorporated in polyimide orienting layers and subsequently irradiated with polarized light. Liquid crystals, which are in contact with the surface of a thus-irradiated layer, are orientated correspondingly to this preferred direction. This orienting procedure is reversible, i.e. by repeated irradiation of the layer with light of a second polarization direction the already inscribed direction of orientation is again reversed. Since this re-orientation procedure can arbitrarily be repeated frequently, orienting layers on this basis are less suitable for use in LCD's.

A further possibility for the production of a high resolution orienting pattern in liquid crystal layers is described in Jpn. J. Appl. Phys. Vol. 31 (1992), 2155. In this procedure the dimerization of polymer-bonded photoreactive cinnamic acid groups induced by irradiation with linear polarized light is used for the structured orienting of liquid crystals. In contrast to the above-described reversible orienting procedure, an anisotropic polymer network is produced in the photo-structurable orienting layers described in Jpn. J. Appl. Phys. Vol. 31 (1992), 2155. These photo-orientable polymer networks are primarily usable where structured or non-structured liquid crystal orienting layers are required. Apart from use in LCD's, such orienting layers can also be used, for example, for the production of so-called hybrid layers as are exemplified in European Patent Applications EP-A-0 611 981, EP-A-0 689 084, EP-A-0 689 065 and EP-A-0 753 785. Optical elements such as, for example, non-absorptive color filters, linear and circular polarizers, optical delay layers, etc. can be realised using these hybrid layers of photo-structured orienting polymers and cross-linkable lower molecular liquid crystals.

Cinnamic acid polymers, which are suitable in principle for the production of such anisotropic cross-linked, photo-structured orienting layers for liquid crystals, are described in EP-A-611,786. These cross-linkable cinnamic acid derivatives are basically linked via the carboxyl function of the cinnamic acid (phenylacrylic acid) and a spacer to the main chain of the polymer. In these polymers the dimerizable acrylic ester group of the cinnamic acid is always aligned "inwards" to the spacer or polymer backbone, while the aromatic residue is always oriented "outwards" from the polymer backbone.

It has now been found that this type of cinnamic acid alignment in known photopolymers is by no means optimal. Concurrent photochemical reactions disturb the orienting capacity. The known cinnamic acid polymers have an inadequate photochemical long-term stability. For example, a lengthy UV light irradiation of a pre-produced orienting layer leads to the destruction of the originally present orientation. Multiple irradiations, in which an already present orienting layer having a predetermined inscribed pattern is irradiated once more in order to orientate the still non-irradiated regions in another direction, can only be carried out when the previously irradiated sites are covered by a mask. On the other hand, the already oriented regions of the layer can lose their structure wholly or in part by photochemical side-reactions.

A further disadvantage of the previously used cinnamic acid polymers is that no tilt angle occurs in the case of orienting surfaces produced from these materials by a simple irradiation with polarized light. In particular, for use in LCD's the orienting layer must produce a tilt angle in addition to the orienting direction.

In the case of the aforementioned uniaxially rubbed polymer orienting layers this tilt angle is already produced by the rubbing procedure on the polymer surface. When a liquid crystal is brought into contact with such a surface, then the liquid crystal molecules lie not parallel, but inclined to the surface, with the tilt angle thus being conferred to the liquid crystal. The size of the tilt angle is thus determined not only by rubbing parameters such as, for example, feed velocity and contact pressure, but also by the chemical structure of the polymer. A tilt angle between 1° and 15° is required for the production of liquid crystal indicators depending on type. The largest tilt angles are required especially for Supertwisted Nematic (STN) LCD's in order to avoid the occurrence of so-called fingerprint textures. In TN and TFT-TN LCD's the direction of rotation and the direction of tilt is defined by the tilt angle, whereby "reverse twist" and "reverse tilt" phenomena are prevented. While reverse twist in the unswitched state gives rise to fields having a false sense of direction, which is noticeable optically in a speckled appearance of the indicator, reverse tilt is noticeable optically to a very disturbing extent primarily upon switching the LCD's by tilting the liquid crystal in different directions. Reverse twist can be prevented by doping the liquid crystal mixture with a chiral dopant having a suitable direction of rotation. However, in order to suppress reverse tilt there has hitherto been no alternative possibility to the use of orienting layers having a tilt angle.

Cinnamic acid esters which are not, as described above, bonded to a polymer backbone, but which are linked via the spacer with a trialkoxysilane group have recently been reported in Liq. Cryst. 20, 171 (1996). In this case, the trialkoxysilane group serves to anchor the cinnamic acid unit to the substrate as a carrier, for example to glass. The spacer, which links the trialkoxysilane group with the cinnamic acid ester, is thereby always situated in the 2-position (ortho-position) of the cinnamic acid ester. For the production of the orienting layer, the trialkoxysilanes are firstly applied from a solution to the glass carrier. Thereafter, the orientation is effected by irradiation with linear polarized light of 259 nm wavelength. The capacity of the thus-prepared layer to orient liquid crystals is ascribed to a reversible Z/E isomerization. On the other hand, when the cinnamic acid molecules are irradiated at 330 nm, they become cross-linked. Thereby, the orientation capacity is lost in proportion to the degree of cross-linkage.

The orienting layers produced in this manner have the same disadvantages which the cinnamic acid polymers described above have. Also, they have an insufficient photochemical and thermal stability, since the Z/E isomerization is reversible and therefore leads to problems of re-orientation in the case of multiple irradiation. Moreover, they do not also have the capability of inducing a tilt angle.

SUMMARY OF THE INVENTION

The object of the present invention is accordingly to produce photoreactive silanes which do not have the above-described disadvantages of the previously used cinnamic acid polymers and silanes, i.e. the lack of photochemical long-term stability and primarily the lack of a tilt angle after irradiation with polarized light, and thus which are capable of producing a stable highly resolved orienting pattern.

It has surprisingly been found that silanes which are linked via a spacer with 3-aryl-acrylic acid derivatives as the photoreactive unit not in the 2-position (ortho) but in the 3- or 4-position with the aromatic ring fulfill this requirement and are outstandingly suitable as orienting layers for liquid crystals. The cross-linkage of these compounds with linear polarized light leads to a significantly increased photochemical stability of the orienting layer and simultaneously to an excellent orienting of the liquid crystal, which is featured, for example, by a very good contrast. Moreover, tilt angles can be produced upon irradiation with linear polarized light.

DETAILED DESCRIPTION OF THE INVENTION

The present invention provides silanes of general formula I:

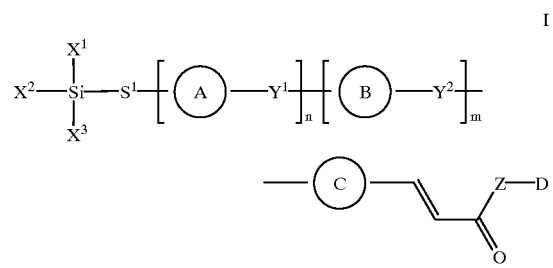

wherein
$X^1$, $X^2$ and $X^3$ are alkyl, alkoxy or halogen, and at least one of these residues is either alkoxy or halogen;

$S^1$ is a spacer unit, such as a straight-chain or branched alkylene grouping represented hereinafter by —$(CH_2)_r$—, which is optionally substituted by one or more fluorine, chlorine or cyano substituents, or a chain of the formula-$(CH_2)_r$—$L^1$—$(CH_2)_s$—$L^2$— in which $L^1$ and $L^2$ each independently is a single bond or cross-linking functional groups such as O, COO, OOC, $NR^2$, $NR^2$—CO, CO—$NR^2$, $NR^2$—COO, O—CO—$NR^2$, CH=CH or C≡C and $R^2$ is hydrogen or lower alkyl;

r and s are each a whole number of 1 to 20, with the proviso that r+s≦20;

ring A is phenylene which is unsubstituted or optionally substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl or piperazine-1,4-diyl;

ring B is phenylene which is unsubstituted or optionally substituted with fluorine, chlorine, cyano, alkyl or alkoxy, pyridine-2,5-diyl, pyrimidine-2,5-diyl, 1,4- or 2,6-naphthylene, 1,3-dioxane-2,5-diyl or cyclohexane-1,4-diyl;

$Y^1$, $Y^2$ each independently is a single covalent bond, —$(CH_2)_t$—, —O—, —CO—, —CO—O—, —O—OC—, —$NR^3$—, —CO—$NR^3$—, —$R^3N$—CO—, —$(CH_2)_u$—O—, —O—$(CH_2)_u$—, —$(CH_2)_u$—$NR^3$— or —$NR^3$—$(CH_2)_u$—, wherein $R^3$ is hydrogen or lower alkyl;
t is a whole number of 1 to 4;
u is a whole number of 1 to 3;
m, n each independently is 0 or 1;

ring C is phenylene which is unsubstituted or optionally substituted with fluorine, chlorine, cyano, alkyl or alkoxy, pyrimidine-2,5- or 3,5-diyl, pyridine-2,5- or -2,4-diyl or -2,6-diyl, 2,5-thiophenylene, 2,5-furanylene or 1,4- or 2,6-naphthylene; and Z is —O— or —$NR^4$—, in which $R^4$ is hydrogen or lower alkyl or a second group of formula D, in which D is straight-chain or branched alkyl with 1 to 20 carbon atoms optionally substituted with fluorine or chlorine or a cycloalkyl residue with 3 to 8 ring atoms optionally substituted with fluorine, chlorine, alkyl or alkoxy.

The silane derivatives in accordance with the invention can be used individually or in mixtures for the formation or orienting layers. As components for such mixtures there can also be used, in addition to one or more further compounds of formula I, other cross-linkable silane derivatives which are usual for the silanization of inorganic, oxide-containing surfaces, for example with silane derivatives of the general formula $$X^2-\underset{\underset{X^3}{|}}{\overset{\overset{X^1}{|}}{Si}}-S^1-M \qquad II$$

wherein $X^1$, $X^2$, $X^3$ and $S^1$ are defined as set forth above and M is a mesogenic residue or lower alkyl or alkoxy. Such mixtures, which contain at least one component of general formula I, are also an object of the present invention.

The term "mesogenic residue" is in the scope of the present invention a group corresponding to general formula III $$-\!\!\left[\!\!\left(\!A^1\!\right)\!\!-\!Y^1\right]_n\!\!\left[\!\left(\!A^2\!\right)\!-\!Y^2\right]_m\!\!\left(\!A^3\!\right)\!-\!Q \qquad III$$

wherein rings $A^1$, $A^2$ and $A^3$ each independently is phenylene which is unsubstituted or optionally substituted with fluorine, chlorine, cyano, alkyl or alkoxy, pyridine-2,5-diyl, pyrimidine-2,5-diyl, 2,6-naphthylene, 1,3-dioxane-2,5-diyl or cyclohexane-1,4-diyl, with a maximum of one of the rings being different from phenylene or cyclohexylene;

Q is lower alkyl or alkoxy in which one or more hydrogen atoms can be replaced by fluorine, fluorine, chlorine, cyano or nitro; and n, m as well as $Y^1$, $Y^2$ are the same as defined above.

M in the mixture components of formula II preferably is lower alkyl or alkoxy or a mesogenic residue of formula III in which n stands for 0 and m stands for 0 or 1. Further, those mesogenic residues of general formula III in which n stands for 0 and rings $A^2$ and $A^3$ each independently is phenylene or cyclohexylene, $Y^2$ is a single covalent bond, —CH$_2$CH$_2$—, —O—, —CH$_2$—O—, —O—CH$_2$—, —CO—O— or —O—OC— and Q is lower alkyl or alkoxy (optionally substituted by fluorine), fluorine, chlorine or cyano are preferred.

Quite particularly preferred are those mixture components of formula II in which M is lower alkyl, alkoxy or a residue of formula III in which m and n stand for 0 and Q is lower alkyl or alkoxy optionally substituted with fluorine.

In the mixtures in accordance with the invention, the content of silane derivatives which do not correspond to a structure of formula I is smaller than or equal to 50%, preferably smaller than or equal to 30%, and especially smaller than or equal to 15%.

The use of silane derivatives and mixtures in accordance with the invention for the production of orienting layers for liquid crystals as well as their use in optical components, especially for the production of hybrid layer elements, are also objects of the present invention.

The term "lower alkyl" taken alone or in combination such as in "lower alkoxy" denotes straight-chain and branched saturated hydrocarbon residues with 1 to 6, preferably with 1 to 3, carbon atoms, such as methyl, ethyl, propyl or i-propyl and the like.

The term "alkyl" taken alone or in combination such as in "alkoxy" denotes straight-chain and branched saturated hydrocarbon residues with up to 30 carbon atoms.

Preferred "spacer units" in the scope of the present invention are a straight-chain or branched alkylene grouping represented by —(CH$_2$)$_r$—, as well as —(CH$_2$)$_r$—O—, —(CH$_2$)$_r$—O—(CH$_2$)$_s$—, —(CH$_2$)$_r$—COO—(CH$_2$)$_s$—, —(CH$_2$)$_r$—OOC—(CH$_2$)$_s$—, —(CH$_2$)$_r$—NR$^2$—CO—(CH$_2$)$_s$—, —(CH$_2$)$_r$—NR$^2$—COO—(CH$_2$)$_s$—, —(CH$_2$)$_r$—O—(CH$_2$)$_s$—O—, —(CH$_2$)$_r$—COO—(CH$_2$)$_s$—O—, —(CH$_2$)$_r$—OOC—(CH$_2$)$_s$—O—, —(CH$_2$)$_r$—NR$^2$—CO—(CH$_2$)$_s$—O—, —(CH$_2$)$_r$—NR$^2$—COO—(CH$_2$)$_s$—O—, —(CH$_2$)$_r$—CO—, —(CH$_2$)$_r$—CO—O—, —(CH$_2$)$_r$—O—CO—, —(CH$_2$)$_r$—CO—NR$^2$— or —(CH$_2$)$_r$—NR$^2$—CO— in which r and s each are a whole number of 1 to 20, especially 2 to 12, with the proviso that r+s≦20, especially 15; and in which $R^2$ is hydrogen or lower alkyl.

Examples of preferred "spacer units" are 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,3-butylene, 3-methyl-1,3-butylene, proyleneoxy, propyleneoxycarbonyl, propyleneoyloxy, butyleneoxy, butyleneoxycarbonyl, butyleneoyloxy, pentyleneoxy, pentylenoxycarbonyl, pentyleneoyloxy, hexyleneoxy, hexyleneoxycarbonyl, hexyleneoyloxy, heptyleneoxy, heptyleneoxycarbonyl, heptyleneoyloxy, octyleneoxy, octyleneoxycarbonyl, octyleneoyloxy, nonyleneoxy, nonyleneoxycarbonyl, nonyleneoyloxy, decyleneoxy, decyleneoxycarbonyl, decyleneoyloxy, undecyleneoxy, undecyleneoxycarbonyl, undecyleneoyloxy, dodecyleneoxy, dodecyleneoxycarbonyl, dodecyleneoyloxy, propyleneaminocarbonyl, butyleneaminocarbonyl, pentyleneaminocarbonyl, hexyleneaminocarbonyl, heptyleneamino-carbonyl, octyleneaminocarbonyl, nonyleneaminocarbonyl, decyleneaminocarbonyl, undecyleneaminocarbonyl, dodecyleneaminocarbonyl, propylenecarbonylamino, butylenecarbonylamino, pentylenecarbonylamino, hexylenecarbonylamino, heptylenecarbonylamino, octylenecarbonylamino, nonylenecarbonylamino, decylenecarbonylamino, undecylenecarbonylamino, dodecylenecarbonylamino, propylenecarbamoyloxyhexylene, 3-propyleneoxy-6-hexylene, 3-propyleneoxy-6-hexyleneoxy, propylenecarbamoyloxyhexyloxy, propylenecarbamoylhexylene, propylenecarbamoylhexyloxy and the like.

Especially preferred "spacer units" are a straight-chain alkylene grouping represented by —(CH$_2$)$_r$—, as well as —(CH$_2$)$_r$—O—, —(CH$_2$)$_r$—NH—CO—(CH$_2$)$_s$—, —(CH$_2$)$_r$—NH—COO—(CH$_2$)$_s$—, —(CH$_2$)$_r$—O—(CH$_2$)$_s$—O—, —(CH$_2$)$_r$—NH—CO—(CH$_2$)$_s$—O—, —(CH$_2$)$_r$—NH—COO—(CH$_2$)$_s$—O—, —(CH$_2$)$_r$—CO—O—, —(CH$_2$)$_r$—O—CO—, —(CH$_2$)$_r$—CO—NH— or —(CH$_2$)$_r$—NH—CO— in which r and s are each a whole number of 2 to 12 and the sum of r+s<15.

The term "phenylene which is unsubstituted or optionally substituted with fluorine, chlorine, cyano, alkyl or alkoxy" embraces in the scope of the present invention 1,3- or 1,4-phenylene which is unsubstituted or mono- or multiply-substituted with fluorine, chlorine, cyano, alkyl or alkoxy, preferably with fluorine, methyl, ethyl, propyl, butyl, methoxy, ethoxy, propoxy, butoxy or cyano.

Examples of preferred phenylene residues are 1,3- or 1,4-phenylene, 4- or 5-methyl-1,3-phenylene, 4- or 5-methoxy-1,3-phenylene, 4- or 5-ethyl-1,3-phenylene, 4- or 5-ethoxy-1,3-phenylene, 2- or 3-methyl-1,4-phenylene, 2- or 3-ethyl-1,4-phenylene, 2- or 3-propyl-1,4-phenylene, 2- or 3-butyl-1,4-phenylene, 2- or 3-methoxy-1,4-phenylene, 2- or 3-ethoxy-1,4-phenylene, 2- or 3-propoxy-1,4-phenylene, 2- or 3-butoxy-1,4-phenylene, 2,3-, 2,6- or 3,5-dimethyl-1,4-phenylene, 2,6- or 3,5-dimethoxy-1,4-phenylene, 2- or 3-fluoro-1,4-phenylene, 2,3-, 2,6- or 3,5-difluoro-1,4-phenylene, 2- or 3-chloro-1,4-phenylene, 2,3-, 2,6- or 3,5-dichloro-1,4-phenylene, 2- or 3-cyano-1,4-phenylene and the like.

Preferably, in the compounds of formula I ring A is phenylene which is unsubstituted or optionally substituted with fluorine, chlorine, cyano, alkyl or alkoxy, pyridine-2,5-diyl, pyrimidine-2,5-diyl or cyclohexane-1,4-diyl;

ring B is phenylene which is unsubstituted or optionally substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$ each independently is a single covalent bond, —CH$_2$CH$_2$—, —O—, —CH$_2$—O—, —O—CH$_2$—, —CO—O— or —O—OC—;

m, n each independently is 0 or 1;

ring C is 1,3- or 1,4-phenylene which is unsubstituted or optionally substituted with fluorine, chlorine, cyano, alkyl or alkoxy, pyrimidine-2,5-diyl, pyridine-2,5-diyl, 2,5-furanylene or 1,4- or 2,6-naphthylene;

Z is —O—;

D is straight-chain or branched alkyl with 1 to 20 carbon atoms or a cycloalkyl residue with 5 or 6 ring atoms optionally substituted with alkyl or alkoxy, especially with methyl or methoxy; and $S^1$ is the same as in formula I.

Especially preferred are those silane derivatives of formula I in which n is 0 ring B is phenylene which is unsubstituted or optionally substituted with fluorine, chlorine, cyano, alkyl or alkoxy, pyridine-2,5-diyl, pyrimidine-2,5-diyl or cyclohexane-1,4-diyl;

$Y^2$ is a single covalent bond, —CO—O— or —O—OC—;

m is 0 or 1;

ring C is 1,3- or 1,4-phenylene which is unsubstituted or optionally substituted with fluorine, chlorine, cyano, alkyl or alkoxy or 1,4- or 2,6-naphthylene;

Z is —O—;

D is straight-chain or branched alkyl with 1 to 12 carbon atoms; and $S^1$ is the same as in formula I.

The silane derivatives of formula I can be prepared by methods known to a person skilled in the art. Thus, for example, precursors to the compounds of formula I which have a terminal double bond in place of the silane group at the end of the spacer S1 can be reacted with commercially available silanes of the formula $X^1X^2X^3SiH$ by hydrosilylation to give the compounds of formula I. A further preparative method comprises reacting a silane of the formula $X^1X^2X^3Si$—$(CH_2)_r$—N=C=O with a hydroxy or amino compound in which the hydroxyl group or the amino group is situated at the desired linkage site in the spacer or on the ring linked with the spacer. There are thus obtained those compounds of formula I which have a N—CO—O— or, respectively, N—CO—N— grouping in the spacer or at the linkage site with ring. On the other hand, by reaction of the aforementioned hydroxy or amino compounds with silanes of the formula $X^1X^2X^3Si$—$(CH_2)_r$—Br there can be prepared those compounds of formula I which contain an ether function or an alkylamino group in the spacer or at the linkage site with the ring. By reaction with silanes of the formula $X^1X^2X^3Si$—$(CH_2)_r$—$NHR^2$ using an acid chloride there can be prepared those silanes of formula I which have a $NR^2CO$ group in the spacer or at the linkage site with the ring. Such preparative methods have been described on the basis of analogous examples in U.S. Pat. No. 4,918,200 and U.S. Pat. No. 4,861,906.

The silane precursors are for the most part commercially available or can be modified readily from commercially available silane building bricks. The cinnamic acids are, in part, also commercially available or can be obtained according to processes known from the literature such as, for example, the Knoevenagel reaction or the Wittig reaction, from commercially available aldehydes, or from cyano compounds by previous reduction to the corresponding aldehydes. The cinnamic acid esters or amides can be prepared from cinnamic acids according to known esterification methods.

In order to prepare orienting layers, the silane derivatives or mixtures in accordance with the invention must initially be applied to a carrier. As a result, the silane groups are bonded as coupling units to the carrier and form particularly thin, often monomolecular layers. Such silanizations of different, mostly inorganic oxides are widespread in practice and will be well known to a person skilled in the art. Examples of known carrier materials are aluminium oxide, titanium oxide, silicon oxide (glass or quartz) or mixed oxides such as, for example, indium-tin oxide (ITO).

In the case of the uses in accordance with the invention for optical or electro-optical devices, there stand in the foreground as carrier materials primarily glass or an optionally electrode-coated carrier, e.g. a glass plate coated with indium-tin oxide (ITO). For the application, the silane derivatives are predominantly used as solutions in an inert solvent. Depending on the reactivity of the silane group, a large number of different solvents can be used, such as, for example, benzene, toluene, hexane etc., or, in the case of the less reactive alkoxysilanes, alcohols such as methanol, ethanol and the like. The subsequent coating can be effected, for example, by immersing the cleaned carrier in the solution, by spin-coating or by other coating techniques. After evaporation of the solvent from the carrier layer, the coupling of the silane group to the carrier is effected depending on reactivity mainly by heating the impregnated carrier. Subsequently, the non-bound silane content can be washed off with solvents.

The layers, which have been produced from silane derivatives of formula I or from mixtures containing silane derivatives of formula I in this manner or an analogous manner, can be dimerised by irradiation with linear polarized light. By the spatially selective irradiation of the molecular units of formula I coupled to the carrier, quite specific regions on a surface can now be directed and simultaneously also stabilized by the dimerisation.

Thus, for the production of orienting layers in selective regions limited by area, the regions to be oriented can be irradiated with a mercury high pressure lamp, a xenon lamp or a pulsed UV laser using a polarizer and optionally a mask for the definition of structures. The irradiation period depends on the power of the individual lamps and can vary from a few minutes to several hours. However, the dimerization can also be effected by irradiation of the homogeneous layer using filters which, for example, let through only the radiation which is suitable for the cross-linkage reaction.

EXAMPLES

The silanes in accordance with the invention are illustrated in more detail by the following Examples.

Example 1

Methyl (E)-3-[3-methoxy-4-(4-triethoxysilanylbutyloxy)phenyl]acrylate

Air is conducted for 30 min. into a mixture of 1.4 g of 3-methoxy-4-[(E)2-methoxycarbonyl-vinyl]phenyl 4-(3-butenyloxy)benzoate, 0.96 ml of triethoxysilane, 20 ml of toluene and 0.055 ml of platinum divinyltetramethyldisiloxane (3–3.5% in toluene), and the mixture is then stirred at 60° C. for 16 hrs. Alternatively, the air is injected while mixing. The reaction mixture is thereafter cooled to room temperature, partitioned between ethyl acetate and water, and the organic phase is dried over magnesium sulphate, filtered and evaporated to dryness. Chromatography on silica gel with toluene/ethyl acetate (9:1) gives methyl (E)-3-[3-methoxy-4-(4-triethoxysilanylbutyloxy)phenyl]acrylate.

The following silanes can be synthesized in an analogous manner:

Methyl (E)-3-[4-(4-triethoxysilanylbutyloxy)phenyl]acrylate;

methyl (E)-3-[3-fluoro-4-(4-triethoxysilanylbutyloxy)phenyl]acrylate;

methyl (E)-3-[3-ethoxy-4-(4-triethoxysilanylbutyloxy)phenyl]acrylate;

methyl (E)-3-[3-hexyloxy-4-(4-triethoxysilanylbutyloxy)phenyl]acrylate;

methyl (E)-3-[3-(4-triethoxysilanylbutyloxy)phenyl]acrylate;

methyl (E)-3-[4-fluoro-3-(4-triethoxysilanylbutyloxy)phenyl]acrylate;

methyl (E)-3-[4-methoxy-3-(4-triethoxysilanylbutyloxy)phenyl]acrylate;

methyl (E)-3-[4-ethoxy-3-(4-triethoxysilanylbutyloxy)phenyl]acrylate;

methyl (E)-3-[4-hexyloxy-3-(4-triethoxysilanylbutyloxy)phenyl]acrylate;

methyl (E)-3-[4-(8-triethoxysilanyloctyloxy)phenyl]acrylate;

methyl (E)-3-[3-fluoro-4-(8-triethoxysilanyloctyloxy)phenyl]acrylate;

methyl (E)-3-[3-methoxy-4-(8-triethoxysilanyloctyloxy)phenyl]acrylate;

methyl (E)-3-[3-ethoxy-4-(8-triethoxysilanyloctyloxy)phenyl]acrylate;

methyl (E)-3-[3-hexyloxy-4-(8-triethoxysilanyloctyloxy)phenyl]acrylate;

methyl (E)-3-[3-(8-triethoxysilanyloctyloxy)phenyl]acrylate;

methyl (E)-3-[4-fluoro-3-(8-triethoxysilanyloctyloxy)phenyl]acrylate;

methyl (E)-3-[4-methoxy-3-(8-triethoxysilanyloctyloxy)phenyl]acrylate;

methyl (E)-3-[4-ethoxy-3-(8-triethoxysilanyloctyloxy)phenyl]acrylate;

methyl (E)-3-[4-hexyloxy-3-(8-triethoxysilanyloctyloxy)phenyl]acrylate;

methyl (E)-3-[4-(6-triethoxysilanylhexanoyloxy)phenyl]acrylate;

methyl (E)-3-[3-fluoro-4-(6-triethoxysilanylhexanoyloxy)phenyl]acrylate;

methyl (E)-3-[3-methoxy-4-(6-triethoxysilanylhexanoyloxy)phenyl]acrylate;

methyl (E)-3-[3-ethoxy-4-(6-triethoxysilanylhexanoyloxy)phenyl]acrylate;

methyl (E)-3-[3-butyloxy-4-(6-triethoxysilanylhexanoyloxy)phenyl]acrylate;

methyl (E)-3-[4-(5-triethoxysilanylpentanoyloxy)phenyl]acrylate;

methyl (E)-3-[4-fluoro-3-(6-triethoxysilanylhexanoyloxy)phenyl]acrylate;

methyl (E)-3-[4-methoxy-3-(6-triethoxysilanylhexanoyloxy)phenyl]acrylate;

methyl (E)-3-[4-ethoxy-3-(6-triethoxysilanylhexanoyloxy)phenyl]acrylate;

methyl (E)-3-[4-butyloxy-3-(6-triethoxysilanylhexanoyloxy)phenyl]acrylate.

Example 2

2-Methoxy-4-[(E)2-methoxycarbonylvinyl]phenyl 4-(4-triethoxysilanylbutyloxy)benzoate Air was conducted for 30 min. into a mixture of 1 g of 2-methoxy-4-[(E)2-methoxycarbonyl-vinyl]phenyl 4-(3-butenyloxy)benzoate, 0.480 ml of triethoxysilane, 10 ml of toluene and 0.017 ml of platinum divinyltetramethyldisiloxane (3–3.5% in toluene) and the mixture was then stirred at 60° C. for 1 hr. Then, a further 0.1 ml of triethoxysilane was added and the mixture was left to react at 60° C. for 16 hrs. The reaction mixture was thereafter cooled to room temperature and partitioned between ethyl acetate and water. The organic phase was thereupon dried over magnesium sulphate, filtered and evaporated to dryness. Chromatography on 150 g of silica gel with toluene/ethyl acetate (19:1 to 9:1) gave 0.60 g of 2-methoxy-4-[(E)2-methoxycarbonyl-vinyl]phenyl 4-(4-triethoxysilanylbutyloxy)benzoate as a colorless liquid, λmax. ($CH_2Cl_2$): 279 nm.

The 2-methoxy-4-[(E)2-methoxycarbonyl-vinyl]phenyl 4-(3-butenyloxy)benzoate used as the starting material was prepared according to the following procedure:

Methyl (E)-4-hydroxy-3-methoxycinnamate 100 g of 4-hydroxy-3-methoxycinnamic acid were dissolved in 1 l of methanol and treated with 14.4 ml of concentrated sulphuric acid. The solution was heated under reflux for 2.5 hrs. Subsequently, the majority of the methanol (about 750 ml) was distilled off and the residue remaining was poured into 1 l of water. Then, the mixture was extracted three times with 500 ml of ethyl acetate each time and the organic phases were combined, washed twice with 250 ml of 10% sodium bicarbonate solution each time, dried over sodium sulphate, filtered and evaporated. The residue was dissolved in 800 ml of methanol, filtered and, for crystallization, cooled to −25° C. The crystals were thereupon filtered off under suction, washed with 100 ml of cold methanol and dried in a high vacuum at room temperature. This gave 54.7 g of yellowish colored crystals.

2-Methoxy-4-[(E)2-methoxycarbonyl-vinyl]-phenyl 4-(3-butenyloxy)benzoate

A mixture of 4.85 g of 4-(3-butenyloxy)benzoic acid and 6 ml of thionyl chloride was treated with 3 drops of dimethylformamide and heated to reflux for 3 hrs. The excess acid chloride was thereupon distilled off firstly at normal pressure and then with increasing vacuum, the residue was held under a high vacuum for 2.5 hrs. and subsequently dissolved in 20 ml of methylene chloride. This solution was added dropwise while cooling with ice to obtain a mixture of 5 g of methyl (E)-4-hydroxy-3-methoxycinnamate, 25 ml of methylene chloride and 3.9 ml of triethylamine and subsequently left to react at room temperature for 60 hrs. Then, the reaction solution was filtered, concentrated slightly and chromatographed over 314 g of silica gel with methylene chloride. Crystallization from cold ethanol gave 7.03 g of 2-methoxy-4-[(E)2-methoxycarbonyl-vinyl]phenyl 4-(3-butenyloxy)benzoate.

The following silane derivatives can be prepared in an analogous manner:

2-Methoxy-4-[(E)2-methoxycarbonyl-vinyl]phenyl 4-(3-triethoxysilanylpropyloxy)benzoate;

2-methoxy-4-[(E)2-methoxycarbonyl-vinyl]phenyl 4-(5-triethoxysilanylpentyloxy)benzoate;

2-methoxy-4-[(E)2-methoxycarbonyl-vinyl]phenyl 4-(6-triethoxysilanylhexyloxy)benzoate;

2-methoxy-4-[(E)2-methoxycarbonyl-vinyl]phenyl 4-(7-triethoxysilanylheptyloxy)benzoate;

2-methoxy-4-[(E)2-methoxycarbonyl-vinyl]phenyl 4-(8-triethoxysilanyloctyloxy)benzoate;

2-methoxy-4-[(E)2-methoxycarbonyl-vinyl]phenyl 4-(4-triethoxysilanylbutyl)benzoate;

2-methoxy-4-[(E)2-methoxycarbonyl-vinyl]phenyl 4-(8-triethoxysilanyloctyl)benzoate;

2-ethoxy-4-[(E)2-methoxycarbonyl-vinyl]phenyl 4-(4-triethoxysilanylbutyloxy)benzoate;

2-propyloxy-4-[(E)2-methoxycarbonyl-vinyl]phenyl 4-(4-triethoxysilanylbutyloxy)benzoate;

2-methoxy-4-[(E)2-ethoxycarbonyl-vinyl]phenyl 4-(8-triethoxysilanyloctyl)benzoate;

2-ethoxy-4-[(E)2-ethoxycarbonyl-vinyl]phenyl 4-(4-triethoxysilanylbutyloxy)benzoate.

Example 3
Methyl (E)-3-{3-methoxy-4-[6-(3-triethoxysilanylpropylcarbamoyloxy)hexyloxy]phenyl}acrylate A mixture of 0.73 g of methyl (E)-3-[3-methoxy-4-(6-hydroxyhexyloxy)phenyl]acrylate, 35 ml of methylene chloride, 0.615 ml of 3-triethoxysilanylpropyl isocyanate and 0.014 ml of dibutyltin dilaurate was heated under reflux for 60 hrs. Thereafter, the reaction solution was cooled, evaporated and the residue was purified by two-fold chromatography on 100 g of silica gel each time, firstly with toluene/ethyl acetate (3:1) and then with cyclohexane/ethyl acetate (7:3). This gave 0.9 g of methyl (E)-3-{3-methoxy-4-[6-(3-triethoxysilanylpropylcarbamoyloxy)hexyloxy]phenyl}acrylate, λmax. (CH$_2$Cl$_2$): 323 nm (ε=19244).

The methyl (E)-3-[3-methoxy-4-(6-hydroxyhexyloxy)phenyl]acrylate used as the starting material was prepared according to the following procedure:
Methyl (E)-3-[3-methoxy-4-(6-hydroxyhexyloxy)phenyl] acrylate A mixture of 0.5 g of methyl (E)-4-hydroxy-3-methoxycinnamate, 10 ml of 2-butanone, 0.35 ml of 6-bromohexanol and 1 g of ground potassium carbonate was heated under reflux for 5 hrs. Then, the reaction mixture was cooled and partitioned between ethyl acetate and water. The organic phase was dried over magnesium sulphate, filtered and evaporated. Chromatography on 100 g of silica gel with toluene/ethyl acetate (1:1) gave 750 ml of methyl (E)-3-[3-methoxy-4-(6-hydroxyhexyloxy)phenyl]acrylate as a colorless solid, λmax. (CH$_2$Cl$_2$): 323 nm (ε=20513).

The following silane derivatives can be prepared in an analogous manner:

Methyl (E)-3-{3-methoxy-4-[5-(3-triethoxysilanylpropylcarbamoyloxy)pentyloxy]phenyl}acrylate;

methyl (E)-3-{3-methoxy-4-[4-(3-triethoxysilanylpropylcarbamoyloxy)butyloxy]phenyl}acrylate;

methyl (E)-3-{3-methoxy-4-[3-(3-triethoxysilanylpropylcarbamoyloxy)propyloxy]phenyl}acrylate;

methyl (E)-3-{3-methoxy-4-[2-(3-triethoxysilanylpropylcarbamoyloxy)ethoxy]phenyl}acrylate;

methyl (E)-3-{4-[6-(3-triethoxysilanylpropylcarbamoyloxy)hexyloxy]phenyl}acrylate;

methyl (E)-3-{3-fluoro-4-[6-(3-triethoxysilanylpropylcarbamoyloxy)hexyloxy]phenyl}acrylate;

methyl (E)-3-{3-ethoxy-4-[6-(3-triethoxysilanylpropylcarbamoyloxy)hexyloxy]phenyl}acrylate;

methyl (E)-3-{3-pentyloxy-4-[6-(3-triethoxysilanylpropylcarbamoyloxy)hexyloxy]phenyl}acrylate;

methyl (E)-3-{2-methoxy-4-[6-(3-triethoxysilanylpropylcarbamoyloxy)hexyloxy]phenyl}acrylate; λmax. (CH$_2$Cl$_2$): 327 nm (ε=18095);

methyl (E)-3-{2-methyl-4-[6-(3-triethoxysilanylpropylcarbamoyloxy)hexyloxy]phenyl}acrylate; (CH$_2$Cl$_2$): 315 nm (ε=18786);

methyl (E)-3-{3-[6-(3-triethoxysilanylpropylcarbamoyloxy)hexyloxy]phenyl}acrylate; λmax. (CH$_2$Cl$_2$): 277 nm (ε=17200);

methyl (E)-3-{4-fluoro-3-[6-(3-triethoxysilanylpropylcarbamoyloxy)hexyloxy]phenyl}acrylate;

methyl (E)-3-{4-methoxy-3-[6-(3-triethoxysilanylpropylcarbamoyloxy)hexyloxy]phenyl}acrylate; λmax. (CH$_2$Cl$_2$): 322 nm (ε=17516);

methyl (E)-3-{4-ethoxy-3-[6-(3-triethoxysilanylpropylcarbamoyloxy)hexyloxy]phenyl}acrylate;

methyl (E)-3-{4-pentyloxy-3-[6-(3-triethoxysilanylpropylcarbamoyloxy)hexyloxy]phenyl}acrylate;

methyl (E)-3-{4'-[6-(3-triethoxysilanylpropylcarbamoyloxy)hexyloxy]biphenyl-4-yl-}acrylate;

methyl trans-(E)-3-{4-[4-[3-(3-triethoxysilanylpropylcarbamoyloxy)propyl]cyclohexyl]phenyl}acrylate;

methyl trans-(E)-3-{4{2-[4-[3-(3-triethoxysilanylpropylcarbamoyloxy)propyl]cyclohexyl]ethyl}phenyl}acrylate;

methyl trans-(E)-3-{4{2-[4-[3-(3-triethoxysilanylpropylcarbamoyloxy)propyl]cyclohexyl]ethoxy}phenyl}acrylate;

methyl (E)-3-{3'-fluoro-4'-[6-(3-triethoxysilanylpropylcarbamoyloxy)hexyloxy]biphenyl-4-yl}acrylate;

methyl (E)-3-{3'-methoxy-4'-[6-(3-triethoxysilanylpropylcarbamoyloxy)hexyloxy]biphenyl-4-yl}acrylate;

methyl (E)-3-{3-fluoro-4'-[6-(3-triethoxysilanylpropylcarbamoyloxy)hexyloxy]biphenyl-4-yl}acrylate;

methyl (E)-3-{3-methoxy-4'-[6-(3-triethoxysilanylpropylcarbamoyloxy)hexyloxy]biphenyl-4-yl}acrylate;

methyl (E)-3-{4'-[6-(3-triethoxysilanylpropylcarbamoyloxy)hexyloxy]biphenyl-3-yl}acrylate;

methyl trans-(E)-3-{3-[4-[6-(3-triethoxysilanylpropylcarbamoyloxy)hexyloxy]cyclohexyl]phenyl}acrylate.

Example 4

Methyl (E)-3-{6-[6-(3-triethoxysilanylpropylcarbamoyloxy)hexyloxy]naphthalen-2-yl}acrylate A mixture of 500 mg of methyl (E)-3-[6-(6-hydroxyhexyloxy)naphthalen-2-yl]acrylate, 25 ml of methylene chloride, 0.376 ml of 3-triethoxysilanylpropyl isocyanate and 0.009 ml of dibutyltin dilaurate was heated under reflux for 3 hrs. Thereafter, a further 0.009 ml of dibutyltin dilaurate was added and the mixture was left to react under reflux for 16 hrs. Then, the reaction solution was cooled to room temperature, evaporated completely and the residue was chromatographed on 150 g of silica gel with ether/hexane. This gave 830 mg of methyl 3-{6-[6-(3-triethoxysilanylpropylcarbamoyloxy)hexyloxy]naphthalen-2-yl}acrylate as a colorless solid, $\lambda$max. ($CH_2Cl_2$): 326 nm ($\epsilon$=26200).

The methyl 3-[6-(6-hydroxyhexyloxynaphthalen-2-yl]acrylate used as the starting material was prepared according to the following procedure:

6-Bromo-2-(6-hydroxyhexyloxy)naphthalene

A mixture of 5 g of 6-bromo-2-naphthol, 50 ml of dimethyl sulphoxide, 3.3 ml of 6-chlorohexanol, 7.1 g of potassium iodide and 7.1 g of potassium carbonate (ground and activated at 80° C. in a high vacuum) was heated to 65° C. for 16 hrs. Then, the mixture was cooled, partitioned between ethyl acetate and water, and the organic phase was washed several times with water, dried over magnesium sulphate, filtered and evaporated. Chromatography of the residue on 200 g of silica gel with toluene/ethyl acetate (3:1) and subsequent crystallization form toluene/hexane (8:1) gave 5.2 g of 6-bromo-2-(6-hydroxyhexyloxy)naphthalene as a colorless solid.

Methyl (E)-3-[6-(6-hydroxyhexyloxy)naphthalen-2-yl]acrylate

A mixture of 5.2 g of 6-bromo-2-(6-hydroxyhexyloxy)naphthalene, 25 ml of triethylamine, 4.3 ml of methyl acrylate, 0.072 g of palladium acetate and 0.392 g of tri-o-tolylphosphine was heated under reflux for 16 hrs. In order to complete the reaction, a further 0.177 g of palladium acetate, 2.5 g of tetrabutylammonium bromide, 10 ml of dimethylformamide and 2 ml of methyl acrylate were added and the mixture was heated to reflux for a further 24 hrs. Thereafter, the reaction mixture was cooled, partitioned between ethyl acetate and water, the organic phase was washed with water, and dried over magnesium sulphate, filtered and evaporated. The residue was chromatographed on 250 g of silica gel with toluene/ethyl acetate (3:1 to 1:1) and subsequently crystallized twice from toluene. This gave 0.63 g of methyl (E)-3-[6-(6-hydroxyhexyloxy)naphthalen-2-yl]acrylate as a colorless solid, $\lambda$max. ($CH_2Cl_2$): 326 nm ($\epsilon$=27660).

The following silanes can be synthesised in an analogous manner:

Methyl (E)-3-{6-[2-(3-triethoxysilanylpropylcarbamoyloxy)ethoxy]naphthalen-2-yl}acrylate;

methyl (E)-3-{6-[3-(3-triethoxysilanylpropylcarbamoyloxy)propyloxy]naphthalen-2-yl}acrylate;

methyl (E)-3-{6-[4-(3-triethoxysilanylpropylcarbamoyloxy)butyloxy]naphthalen-2-yl}acrylate;

methyl (E)-3-{6-[5-(3-triethoxysilanylpropylcarbamoyloxy)pentyloxy]naphthalen-2-yl}acrylate;

methyl (E)-3-{6-[6-(2-triethoxysilanylethylcarbamoyloxy)hexyloxy]naphthalen-2-yl}acrylate;

methyl (E)-3-{4-[2-(3-triethoxysilanylpropylcarbamoyloxy)ethoxy]naphthalen-1-yl}acrylate;

methyl (E)-3-{4-[3-(3-triethoxysilanylpropylcarbamoyloxy)propyloxy]naphthalen-1-yl acrylate;

methyl (E)-3-{4-[4-(3-triethoxysilanylpropylcarbamoyloxy)butyloxy]naphthalen-1-yl}acrylate;

methyl (E)-3-{4-[5-(3-triethoxysilanylpropylcarbamoyloxy)pentyloxy]naphthalen-1-yl}acrylate;

methyl (E)-3-{4-[6-(2-triethoxysilanylethylcarbamoyloxy)hexyloxy]naphthalen-1-yl}acrylate.

Example 5

Methyl trans-(E)-3-{4'-[4-(4-triethoxysilanylbutyl)cyclohexyl]biphenyl-4-yl}acrylate This compound was prepared analogously to Example 1 from methyl trans-(E)-3-(4'-[4-(3-butenyl)cyclohexyl]biphenyl-4-yl}acrylate and triethoxysilane.

The methyl trans-(E)-3-{4'-[4-(3-butenyl)cyclohexyl]biphenyl-4-yl}acrylate used as the starting material was prepared according to the following procedure:

trans-4'-[4-(3-Butenyl)-cyclohexyl]biphenyl-4-carboxaldehyde 38.5 ml of a diIsobutylaluminium hydride solution (20% in toluene) were added dropwise within 10 minutes at 0° C. to a suspension of 11.5 g of trans-4'-[4-(3-butenyl)-cyclohexyl]-biphenyl-4-carbonitrile, prepared according to Mol Cryst. Liq. Cryst. 131, 327 (1985), in 150 ml of toluene. Then, the reaction mixture was warmed slowly to room temperature and left to react for a further 3.5 hours. Subsequently, 1N hydrochloric acid was slowly added dropwise and the reaction mixture was stirred for 1 hour and thereupon partitioned between water and methylene chloride. Thereafter, the organic phase was washed several times with water, dried over magnesium sulphate, filtered and evaporated. Crystallization from ethyl acetate/methylene chloride gives trans-4'-[4-(butenyl)-cyclohexyl]biphenyl-4-carboxaldehyde.

Methyl trans-(E)-3-{4'-[4-(3-butenyl)cyclohexyl]biphenyl-4-yl-}acrylate 27.6 ml of a 1.6N butyllithium solution were added dropwise at 0° C. within 10 minutes to a solution of 6.4 ml of trimethyl phosphonoacetate in 50 ml of dry tetrahydrofuran. The mixture was stirred at 0° C. for 1.5 hours and thereafter a solution of 11.5 g of crude trans-4'-[4-(3-butenyl)cyclohexyl]biphenyl-4-carboxaldehyde in 50 ml of dry tetrahydrofuran was added dropwise within 5 minutes at the same temperature. Subsequently, the mixture was warmed slowly to room temperature and left to react for 15 hours. The reaction mixture was then partitioned between methylene chloride and 1N hydrochloric acid and the organic phase was washed with saturated sodium bicarbonate solution and water, dried over magnesium sulphate and evaporated. Chromatography on silica gel with ethyl acetate/hexane (1:9) and subsequent repeated recrystallization from hexane/ethyl acetate gave methyl trans-(E)-3-{4'-[4-(3-butenyl)cyclohexyl]biphenyl-4-yl}acrylate.

The following silane derivatives can be prepared in an analogous manner:

Methyl trans-(E)-3-{4'-[4-(2-triethoxysilanylethyl)cyclohexyl]biphenyl-4-yl}acrylate;

methyl (E)-3-[4'-(4-triethoxysilanylbutyl)biphenyl-4-yl-]acrylate;

methyl trans-(E)-3-{4-[4-(4-triethoxysilanylbutyl)cyclohexyl]phenyl}acrylate;

methyl trans-(E)-3-{4{2-[4-(4-triethoxysilanylbutyl)cyclohexyl]ethyl}phenyl}acrylate;

methyl trans-(E)-3-{4{2-[4-(4-triethoxysilanylbutyl)cyclohexyl]ethoxy}phenyl}acrylate;

methyl (E)-3-[3'-fluoro-4'-(4-triethoxysilanylbutyl)biphenyl-4-yl]acrylate;

methyl (E)-3-[3'-methoxy-4'-(4-triethoxysilanylbutyl)biphenyl-4-yl]acrylate;

methyl (E)-3-[3-fluoro-4'-(4-triethoxysilanylbutyl)biphenyl-4-yl]acrylate;

methyl (E)-3-[3-methoxy-4'-(4-triethoxysilanylbutyl)biphenyl-4-yl]acrylate;

methyl (E)-3-[4'-(4-triethoxysilanylbutyl)biphenyl-3-yl]acrylate;

methyl trans-(E)-3-{3-[4-(4-triethoxysilanylbutyl)cyclohexyl]phenyl}acrylate.

Example 6
2-Methoxy-4-[(E)2-methoxycarbonylvinyl-]phenyl 4-(4-trichlorosilanylbutyloxy)benzoate 5 ml of trichlorosilane are added while stirring to a solution of 0.1 g of H$_2$PtCl$_6$ in 20 ml of dry tetrahydrofuran. A solution of 14.8 g of 2-methoxy-4-[(E)2-methoxycarbonylvinyl]phenyl 4-(3-butenyloxy)benzoate dissolved in 20 ml of dry tetrahydrofuran is cautiously added dropwise thereto. Thereafter, the mixture is stirred at room temperature for 5 hrs. and then at 50° C. for 16 hrs. The reaction mixture is concentrated in a water-jet vacuum and completely freed from residual solvent and trichlorosilane on an oil pump with a cooling trap under reduced pressure. This gives crude 2-methoxy-4-[(E)2-methoxycarbonylvinyl]phenyl 4-(4-trichlorosilanylbutyloxy)benzoate, which is dissolved in dry tetrahydrofuran for storage.

The 2-methoxy-4-[(E)2-methoxycarbonylvinyl]phenyl 4-(4-trichlorosilanylbutyloxy)benzoate required as the starting material is prepared according to Example 2.

The following silane derivatives can be prepared in an analogous manner:

4-[(E)2-Methoxycarbonylvinyl]phenyl 4-(4-trichlorosilanylbutyloxy)benzoate;

3-[(E)2-methoxycarbonylvinyl]phenyl 4-(4-trichlorosilanylbutyloxy)benzoate;

4-methoxy-3-[(E)2-methoxycarbonylvinyl]phenyl 3-(4-trichlorosilanylbutyloxy)benzoate;

methyl (E)-3-[4-(4-trichlorosilanylbutyloxy)phenyl]acrylate;

methyl (E)-3-[3-fluoro-4-(4-trichlorosilanylbutyloxy)phenyl]acrylate;

methyl (E)-3-[3-methoxy-4-(4-trichlorosilanylbutyloxy)phenyl]acrylate;

methyl (E)-3-[3-ethoxy-4-(4-trichlorosilanylbutyloxy)phenyl]acrylate;

methyl (E)-3-[3-butyloxy-4-(4-trichlorosilanylbutyloxy)phenyl]acrylate;

methyl (E)-3-[3-(4-trichlorosilanylbutyloxy)phenyl]acrylate;

methyl (E)-3-[4-fluoro-3-(4-trichlorosilanylbutyloxy)phenyl]acrylate;

methyl (E)-3-[4-methoxy-3-(4-trichlorosilanylbutyloxy)phenyl]acrylate;

methyl (E)-3-[4-ethoxy-3-(4-trichlorosilanylbutyloxy)phenyl]acrylate;

methyl (E)-3-[4-pentyloxy-3-(4-trichlorosilanylbutyloxy)phenyl]acrylate;

methyl (E)-3-[4-(8-trichlorosilanyloctyloxy)phenyl]acrylate;

methyl (E)-3-[3-fluoro-4-(8-trichlorosilanyloctyloxy)phenyl]acrylate;

methyl (E)-3-[3-methoxy-4-(8-trichlorosilanyloctyloxy)phenyl]acrylate;

methyl (E)-3-[3-ethoxy-4-(8-trichlorosilanyloctyloxy)phenyl]acrylate;

methyl (E)-3-[3-pentyloxy-4-(8-trichlorosilanyloctyloxy)phenyl]acrylate;

methyl (E)-3-[3-(8-trichlorosilanyloctyloxy)phenyl]acrylate;

methyl (E)-3-[4-fluoro-3-(8-trichlorosilanyloctyloxy)phenyl]acrylate;

methyl (E)-3-[4-methoxy-3-(8-trichlorosilanyloctyloxy)phenyl]acrylate;

methyl (E)-3-[4-ethoxy-3-(8-trichlorosilanyloctyloxyphenyl]acrylate;

methyl (E)-3-[4-butyloxy-3-(8-trichlorosilanyloctyloxy)phenyl]acrylate;

methyl (E)-3-[4-(6-trichlorosilanylhexanoyloxy)phenyl]acrylate;

methyl (E)-3-[3-fluoro-4-(6-trichlorosilanylhexanoyloxy)phenyl]acrylate;

methyl (E)-3-[3-methoxy-4-(6-trichlorosilanylhexanoyloxy)phenyl]acrylate;

methyl (E)-3-[3-ethoxy-4-(6-trichlorosilanylhexanoyloxy)phenyl]acrylate;

methyl (E)-3-[3-butyloxy-4-(6-trichlorosilanylhexanoyloxy)phenyl]acrylate;

methyl (E)-3-[4-(5-trichlorosilanylpentanoyloxy)phenyl]acrylate;

methyl (E)-3-[4-fluoro-3-(6-trichlorosilanylhexanoyloxy)phenyl]acrylate;

methyl (E)-3-[4-methoxy-3-(6-trichlorosilanylhexanoyloxy)phenyl]acrylate;

methyl (E)-3-[4-ethoxy-3-(6-trichlorosilanylhexanoyloxy)phenyl]acrylate;

methyl (E)-3-[4-butyloxy-3-(6-trichlorosilanylhexanoyloxy)phenyl]acrylate;

methyl (E)-3-[4'-(4-trichlorosilanylbutyloxy)biphenyl-4-yl]acrylate;

methyl trans-(E)-3-{4-[4-(4-trichlorosilanylbutyl)cyclohexyl]phenyl}acrylate;

methyl trans-(E)-3-{4{2-[4-(4-trichlorosilanylbutyl)cyclohexyl]ethyl}phenyl}acrylate;

methyl trans-(E)-3-{4{2-[4-(4-trichlorosilanylbutyl)cyclohexyl]ethoxy}phenyl}acrylate;

methyl (E)-3-[3'-fluoro-4'-(4-trichlorosilanylbutyloxy)biphenyl-4-yl]acrylate;

methyl (E)-3-[3'-methoxy-4'-(4-trichlorosilanylbutyloxy)biphenyl-4-yl]acrylate.

Example 7
Production of a Photo Cross-linkable Layer 0.02 g of methyl 3-{6-[6-(3-triethoxysilanylpropylcarbamoyloxy)hexyloxy]naphthalen-2-yl}acrylate was dissolved in 2 ml of the solvent mixture of toluene and ethanol (1:1). A cleaned glass plate (19×26 mm) was immersed in this solution for 30 min. and thereafter tempered at a temperature of 100° C. for a further 30 min. Thereupon, the thus-treated glass plate was cleaned in toluene for 10 min. in an ultrasound bath.

Example 8
Production of an Orienting Layer for Liquid Crystals

The coated glass plate described in Example 7 was irradiated for three minutes with the linear polarized UV light from a mercury high pressure lamp. Thereafter, a liquid crystal layer was applied to the irradiated layer by spin-coating. Under a polarization microscope there could thereupon be observed a uniaxial doubly refracting layer of oriented liquid crystal molecules. With the aid of a tilt compensator it was established that the direction of orientation corresponds to the direction of polarization of the UV light used to irradiate the silane layer.

Example 9
Production of an Orienting Layer having a Defined Tilt Angle

Two glass plates coated according to Example 7 with methyl 3-{6-[6-(3-triethoxysilanylpropylcarbamoyloxy)hexyloxy]naphthalen-2-yl}acrylate were irradiated with linear polarized UV light for 9 min., with the direction of incidence of the light being inclined by 70° to the plate normal. The direction of polarization of the light thus lay in the plain extending between the direction of incidence of the light and the plate normal. The two plates were thereafter brought together with the irradiated sides facing inwards to give a liquid crystal cell having a plate separation of 20 μm such that the featured directions produced upon irradiating the plates by polarization and light incidence were parallel to each other. Then, the cell was filled with the liquid crystal mixture 3010 of ROLIC AG at a temperature of 100° C., with the liquid crystal mixture being in the isotropic phase during the filling operation. Thereupon, the cell was cooled gradually to room temperature at a rate of 1° C./min. A uniformly oriented liquid crystal layer was now recognised between cross polarizers. The tilt angle of this parallel cell was 1.3° measured with the aid of the crystal rotation method.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:

1. A silane compound of general formula I

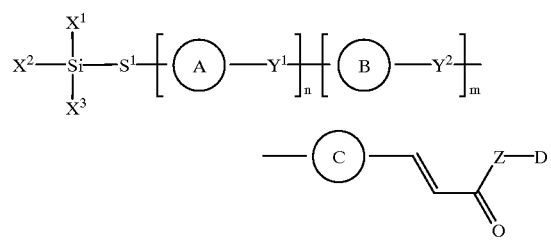

wherein $X^1$, $X^2$ and $X^3$ are alkyl, alkoxy or halogen, at least one of which is either alkoxy or halogen;

$S^1$ is a straight-chain or branched alkylene grouping having a formula —(CH$_2$)$_r$—, which is unsubstituted or substituted by one or more fluorine, chlorine or cyano substituents, or is a chain having a formula-(CH$_2$)$_r$—L$^1$—(CH$_2$)$_s$—L$^2$— in which $L^1$ and $L^2$ each independently is a single bond or cross-linking functional group selected from the group consisting of O, COO, OOC, NR$^2$, NR$^2$—CO, CO—NR$^2$, NR$^2$—COO, O—CO—NR$^2$, CH=CH and C≡C wherein $R^2$ is hydrogen or lower alkyl;

r and s are each a whole number of 1 to 20 wherein r+s≦20;

ring A is 1,3- or 1,4-phenylene and is unsubstituted or substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl or piperazine-1,4-diyl;

ring B is 1,3- or 1,4-phenylene and is unsubstituted or substituted with fluorine, chlorine, cyano, alkyl or alkoxy, pyridine-2,5-diyl, pyrimidine-2,5-diyl, 1,4- or 2,6-naphthylene, 1,3-dioxane-2,5-diyl or cyclohexane-1,4-diyl;

$Y^1$, $Y^2$ each independently is a single covalent bond, —(CH$_2$)$_t$—, —O—, —CO—, —CO—O—, —O—OC—, —NR$^3$—, —CO—NR$^3$—, —R$^3$N—CO—, —(CH$_2$)$_u$—O—, —O—(CH$_2$)$_u$—, —(CH$_2$)$_u$—NR$^3$— or —NR$^3$—(CH$_2$)$_u$—, wherein $R^3$ is hydrogen or lower alkyl;

t is a whole number of 1 to 4;

u is a whole number of 1 to 3;

m, n each independently is 0 or 1;

ring C is 1,3- or 1,4-phenylene which is unsubstituted or substituted with fluorine, chlorine, cyano, alkyl or alkoxy, pyrimidine-2,5- or 3,5-diyl, pyridine-2,5- or -2,4-diyl or -2,6-diyl, 2,5-thiophenylene, 2,5-furanylene or 1,4- or 2,6-naphthylene; and Z is —O— or —NR$^4$—, in which $R^4$ is hydrogen or lower alkyl or a second group of formula D wherein D is straight-chain or branched alkyl with 1 to 20 carbon atoms and is unsubstituted or substituted with fluorine or chlorine or a cycloalkyl residue with 3 to 8 ring atoms which is unsubstituted or substituted with fluorine, chlorine, alkyl or alkoxy.

2. A silane compound according to claim 1, wherein ring A is 1,3- or 1,4-phenylene and is unsubstituted or substituted with fluorine, chlorine, cyano, alkyl or alkoxy, pyridine-2,5-diyl, pyrimidine-2,5-diyl or cyclohexane-1,4-diyl;

ring B is 1,3- or 1,4-phenylene and is unsubstituted or substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$ each independently is a single covalent bond, —$CH_2CH_2$—, —O—, —$CH_2$—O—, —O—$CH_2$—, —CO—O— or —O—OC—;

ring C is 1,3- or 1,4-phenylene and is unsubstituted or substituted with fluorine, chlorine, cyano, alkyl or alkoxy, pyrimidine-2,5-diyl, pyridine-2,5-diyl, 2,5-furanylene or 1,4- or 2,6-naphthylene;

Z is —O—; and

D is straight-chain or branched alkyl with 1 to 20 carbon atoms or a cycloalkyl residue with 5 or 6 ring atoms which is unsubstituted or substituted with alkyl or alkoxy.

3. A silane compound according to claim 1, wherein n is 0;

ring B is 1,3- or 1,4-phenylene and is unsubstituted or substituted with fluorine, chlorine, cyano, alkyl or alkoxy, pyridine-2,5-diyl, pyrimidine-2,5-diyl or cyclohexane-1,4-diyl;

$Y^2$ is a single covalent bond, —CO—O— or —O—OC—;

ring C is 1,3- or 1,4-phenylene and is unsubstituted or substituted with fluorine, chlorine, cyano, alkyl or alkoxy, or 1,4- or 2,6-naphthylene;

Z is —O—; and

D is straight-chain or branched alkyl with 1 to 12 carbon atoms.

4. A silane compound according to claim 3, wherein the compound is selected from the group consisting of methyl (E)-3-[3-methoxy-4-(4-triethoxysilanylbutyloxy) phenyl]acrylate, 3-methoxy-4-[(E)2-methoxycarbonylvinyl]phenyl 4-(4-triethoxy-silanylbutyloxy)benzoate, methyl (E)-3-{2-methoxy-4-[6-(3-triethoxysilanylpropylcarbamoyloxy)hexyloxy]phenyl}acrylate, methyl (E)-3-{6-[6-(3-triethoxysilanylpropylcarbamoyloxy)hexyloxy]naphthalen-2-yl}acrylate, methyl trans-(E)-3-{4'-[4-(4-triethoxysilanylbutyl)cyclohexyl]biphenyl-4-yl}acrylate, and 3-methoxy-4-[(E)2-methoxycarbonylvinyl]phenyl 4-(4-trichlorosilanylbutyloxy)benzoate.

5. A cross-linkable mixture comprising a compound of formula I defined in claim 1.

6. A cross-linkable mixture according to claim 5 further comprising one or more compounds of general formula II

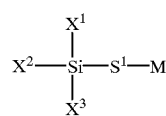

II wherein

M is lower alkyl or alkoxy or a mesogenic residue of general formula III

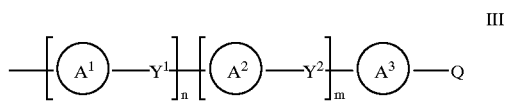

III wherein $A^1$, $A^2$ and $A^3$ each independently is phenylene and is unsubstituted or substituted with fluorine, chlorine, cyano, alkyl or alkoxy, pyridine-2,5-diyl, pyrimidine-2,5-diyl, 2,6-naphthylene, 1,3-dioxane-2,5-diyl or cyclohexane-1,4-diyl, wherein up to one of $A^1$, $A^2$ and $A^3$ is different from phenylene or cyclohexylene; and Q is lower alkyl or alkoxy which is unsubstituted or substituted by fluorine, or is fluorine, chlorine, cyano or nitro.

7. A cross-linkable mixture according to claim 6, wherein n is 0;

m is 0 or 1;

$A^2$ and $A^3$ each independently is phenylene or cyclohexylene;

$Y^2$ is a single covalent bond, —$CH_2CH_2$—, —O—, —$CH_2$—O—, —O—$CH_2$—, —CO—O— or —O—OC—; and Q is lower aikyl or alkoxy optionally substituted with flourine, or is fluorine, chlorine or cyano.

8. A cross-linkable mixture according to claim 7, wherein m is 0;

$A^3$ is phenylene or cyclohexylene; and

Q is lower alkyl or alkoxy and is unsubstituted or substituted with fluorine.

9. A process for preparing orienting layers comprising applying a silane compound according to claim 1 to a carrier to form monomolecular layers.

10. A process according to claim 9 wherein a silane compound according to claim 2 is applied to the carrier.

11. A process according to claim 9 wherein a silane compound according to claim 3 is applied to the carrier.

12. A process according to claim 9 wherein a silane compound according to claim 4 is applied to the carrier.

13. A process for preparing orienting layers comprising applying a mixture according to claim 5 to a carrier to form a monomolecular layer.

14. A process according to claim 13 wherein a mixture according to claim 6 is applied to the carrier.

15. A process according to claim 13 wherein a mixture according to claim 7 is applied to the carrier.

16. A process according to claim 13 wherein a mixture according to claim 8 is applied to the carrier.

* * * * *